US00PP24944P2

(12) United States Plant Patent
Dealtrey

(10) Patent No.: US PP24,944 P2
(45) Date of Patent: Sep. 30, 2014

(54) ***LOBELIA* PLANT NAMED 'SCARLET PRINCESS'**

(50) Latin Name: *Lobelia speciosa*
Varietal Denomination: Scarlet Princess

(71) Applicant: Peter Dealtrey, Maldon (GB)

(72) Inventor: Peter Dealtrey, Maldon (GB)

( * ) Notice: Subject to any disclaimer, the term of this patent is extended or adjusted under 35 U.S.C. 154(b) by 8 days.

(21) Appl. No.: 13/815,646

(22) Filed: Mar. 13, 2013

(51) Int. Cl.
*A01H 5/00* (2006.01)

(52) U.S. Cl.
USPC ..... Plt./451

(58) Field of Classification Search
USPC ..... Plt./451
See application file for complete search history.

*Primary Examiner* — Kent L Bell
(74) *Attorney, Agent, or Firm* — C. A. Whealy

(57) ABSTRACT

A new and distinct cultivar of *Lobelia* plant named 'Scarlet Princess', characterized by its upright and compact plant habit; moderately vigorous growth habit; freely branching habit; dense and bushy plant form; freely flowering habit; long flowering period; dark red-colored flowers; and good garden performance.

1 Drawing Sheet

Botanical designation: *Lobelia speciosa.*
Cultivar denomination: 'SCARLET PRINCESS'.

BACKGROUND OF THE INVENTION

The present invention relates to a new and distinct cultivar of *Lobelia* plant, botanically known as *Lobelia speciosa* and hereinafter referred to by the name 'Scarlet Princess'.

The new *Lobelia* plant is a product of a planned breeding program conducted by the Inventor in Langford, Maldon, Essex, United Kingdom. The objective of the breeding program is to create new compact and uniform *Lobelia* plants with numerous attractive flowers.

The new *Lobelia* plant originated from a cross-pollination made by the Inventor in 2008 of two proprietary seedling selections of *Lobelia speciosa*, not patented. The new *Lobelia* plant was discovered and selected by the Inventor as a single flowering plant within the progeny of the stated cross-pollination in a controlled greenhouse environment in Langford, Maldon, Essex, United Kingdom in 2009.

Asexual reproduction of the *Lobelia* plant by vegetative cuttings in Hillegom, The Netherlands since the summer of 2009 has shown that the unique features of this new *Lobelia* plant are stable and reproduced true to type in successive generations.

SUMMARY OF THE INVENTION

Plants of the new *Lobelia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Scarlet Princess'. These characteristics in combination distinguish 'Scarlet Princess' as a new and distinct *Lobelia* plant:

1. Upright and compact plant habit.
2. Moderately vigorous growth habit.
3. Freely branching habit; dense and bushy plant form.

4. Freely flowering habit.
5. Long flowering period.
6. Dark red-colored flowers.
7. Good garden performance.

Plants of the new *Lobelia* differ primarily from plants of the parent selections in the following characteristics:

1. Plants of the new *Lobelia* are more compact than plants of the parent selections.
2. Plants of the new *Lobelia* grow more uniformly than plants of the parent selections.
3. Plants of the new *Lobelia* have darker-colored leaves than plants of the parent selections.
4. Plants of the new *Lobelia* are more freely flowering than plants of the parent selections.

Plants of the new *Lobelia* can be compared to plants of *Lobelia speciosa* 'Fan Scarlet', not patented. In side-by-side comparisons conducted in Langford, Maldon, Essex, United Kingdom, plants of the new *Lobelia* differed from plants of 'Fan Scarlet' in the following characteristics:

1. Plants of the new *Lobelia* were more compact than plants of 'Fan Scarlet'.
2. Plants of the new *Lobelia* grew more uniformly than plants of 'Fan Scarlet'.
3. Plants of the new *Lobelia* and 'Fan Scarlet' differed in leaf color.
4. Plants of the new *Lobelia* were more freely flowering than plants of 'Fan Scarlet'.

BRIEF DESCRIPTION OF THE PHOTOGRAPH

The accompanying colored photograph illustrates the overall appearance of the new *Lobelia* plant showing the colors as true as it is reasonably possible to obtain in colored reproductions of this type. Colors in the photograph may differ slightly from the color values cited in the detailed botanical description which accurately describe the actual colors of the new *Lobelia* plant.

The photograph comprises a side perspective view of a typical flowering plant of 'Scarlet Princess' grown in an outdoor nursery.

DETAILED BOTANICAL DESCRIPTION

Plants used for the aforementioned photograph and following description were grown during the summer in ground beds in an outdoor nursery in Vogelenzang, The Netherlands and under cultural practices typical of commercial *Lobelia* production. During the production of the plants, day temperatures ranged from 16° C. to 28° C. and night temperatures ranged from 8° C. to 18° C. Plants were two years old when the photograph and the description were taken. In the following description, color references are made to The Royal Horticultural Society Colour Chart, 2007 Edition, except where general terms of ordinary dictionary significance are used.

Botanical classification: *Lobelia speciosa* 'Scarlet Princess'.

Parentage:

*Female, or seed, parent*.—Unnamed proprietary seedling selection of *Lobelia speciosa*, not patented.

*Male, or pollen, parent*.—Unnamed proprietary seedling selection of *Lobelia speciosa*, not patented.

Propagation:

*Type cutting*.—In vitro propagation.

*Time to initiate roots, summer*.—About ten days at temperatures about 20° C.

*Time to initiate roots, winter*.—About twelve days at temperatures about 20° C.

*Time to produce a rooted young plant, summer*.—About four weeks at temperatures about 18° C.

*Time to produce a rooted young plant, winter*.—About five weeks at temperatures about 20° C.

*Root description*.—Thick, fleshy; white in color.

*Rooting habit*.—Freely branching; dense.

Plant description:

*Plant and growth habit*.—Herbaceous perennial; upright and compact plant habit; freely basal branching habit with about three primary flowering stems each with about nine lateral branches developing; relatively short internodes; dense and bushy plant habit; moderately vigorous growth habit.

*Plant height*.—About 66.2 cm.

*Plant width*.—About 30.3 cm.

*Lateral branch description*.—Length: About 22.3 cm. Diameter: About 4 mm. Internode length: About 1.6 cm. Strength: Strong, flexible. Aspect: Mostly upright to about 10° from vertical. Texture: Smooth, glabrous. Color: Close to 166A.

Foliage description:

*Arrangement*.—Alternate, simple; sessile.

*Length*.—About 10.7 cm.

*Width*.—About 2.9 cm.

*Shape*.—Obovate to oblanceolate.

*Apex*.—Acute to long acuminate.

*Base*.—Long and narrowly cuneate.

*Margin*.—Irregularly dentate to serrate.

*Texture, upper and lower surfaces*.—Smooth, glabrous; slightly leathery.

*Venation pattern*.—Pinnate.

*Color*.—Developing leaves, upper surface: Close to 203A tinged with close to 147A. Developing leaves, lower surface: Close to 137A to 137B tinged with close to 203A. Fully expanded leaves, upper surface: Close to between N186C and 200A; towards the base, tinged with close to 137A; venation, close to 200A to 200B. Fully expanded leaves, lower surface: Close to 137B heavily tinged with close to 187B; venation, close to 200A.

Flower description:

*Flower arrangement, habit and shape*.—Single flowers arranged in terminal racemes; flowers held slightly upright to outwardly; freely flowering habit with typically 24 flowers per inflorescence and about 225 flowers developing per plant; flowers bilabiate with two free smaller upper petals and three partially-fused lower petals.

*Inflorescence length*.—About 27 cm.

*Inflorescence diameter*.—About 6.4 cm.

*Fragrance*.—None detected.

*Natural flowering season*.—In The Netherlands, plants of the new *Lobelia* flower continuously from early spring to late summer; plants begin flowering about 13 weeks after planting.

*Flower longevity on the plant*.—Longevity of individual flowers is highly dependent on temperature, flowers typically last about ten days on the plant; flowers not persistent.

*Flower diameter*.—About 2.9 cm by 3.5 cm.

*Flower depth*.—About 3.2 cm.

*Flower buds*.—Length: About 1.8 cm. Diameter: About 5 mm. Shape: Oblong to narrowly obovate. Color: Close to 60B; towards the apex, close to 46A.

*Petals*.—Quantity and arrangement: Single whorl of five petals fused towards the base; two smaller free upper petals and three partially-fused lower petals; all petals fused into a tube towards the base. Length: About 3.8 mm. Width, upper petals: About 5 mm. Width, lower petals: About 9 mm. Shape: Narrowly spatulate. Apex: Narrowly acute. Margin: Entire. Texture, upper surface: Smooth, glabrous; velvety. Texture, lower surface: Smooth, and mostly glabrous; sparsely pubescent along main veins. Color: When opening and fully opened, upper surface: Close to between 45B and 46B; throat, close to 53A to 53C; color does not fade with development. When opening, lower surface: Close to between 46A and 53B; tube, close to 53A to 53B.

*Sepals*.—Quantity and arrangement: Single whorl of five sepals, fused at the base; calyx, campanulate. Length: About 1.5 cm. Width: About 2 mm. Shape: Lanceolate. Apex: Narrowly acute. Base: Broadly cuneate. Margin: Entire. Texture, upper and lower surfaces: Smooth, glabrous. Color: When opening and fully opened, upper surface: Close to N186C slightly tinged with close to 147A. When opening and fully opened, lower surface: Close to N186C.

*Peduncles*.—Length: About 24.6 cm. Diameter: About 3 mm. Strength: Strong, flexible. Texture: Smooth, glabrous. Color: Close to between 166A and 200A.

*Pedicels*.—Length: About 1.3 cm. Diameter: About 2 mm. Aspect: About 10° from peduncle axis. Strength: Moderately strong, flexible. Texture: Smooth, glabrous. Color: Close to 183A to 183B.

*Reproductive organs*.—Stamens: Quantity per flower: Five. Filament length: About 1.9 cm. Filament color: Close to 60A. Anther length: About 3 mm. Anther shape: Narrowly oblong. Anther color: Close to between 156D and 161A. Pollen amount: Scarce. Pollen color: Close to 20B. Pistils: Quantity per flower: One. Pistil length: About 2 cm. Stigma shape: Bilobate. Stigma color: Close to 46A. Style length: About 1.8 cm. Style color: Close to 35B. Ovary color: Close to 46A.

*Fruits and seeds*.—Fruit and seed development have not been observed on plants of the new *Lobelia*.

Disease & pest resistance: Plants of the new *Lobelia* have not been noted to be resistant to pathogens and pests common to *Lobelia* plants.

Garden performance: Plants of the new *Lobelia* have been observed to have good garden performance and to tolerate wind, rain, high temperatures about 40° C. and to be hardy to USDA Hardiness Zone 5.

It is claimed:

1. A new and distinct *Lobelia* plant named 'Scarlet Princess' as illustrated and described.

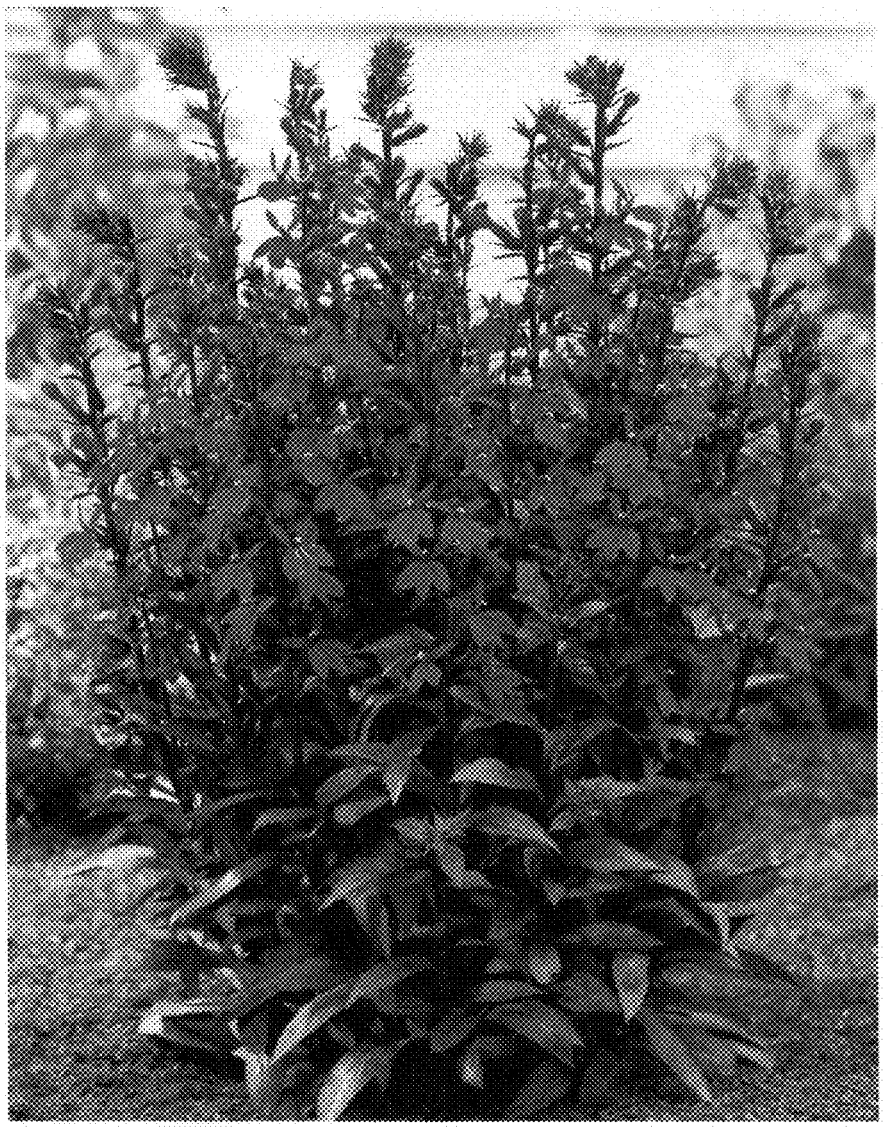

* * * * *